(12) United States Patent
Murray et al.

(10) Patent No.: US 11,202,637 B2
(45) Date of Patent: Dec. 21, 2021

(54) STRETCH HOOP COUPLER FOR RELOADABLE HEMOSTASIS CLIPPING DEVICE

(71) Applicant: BOSTON SCIENTIFIC SCIMED, INC., Maple Grove, MN (US)

(72) Inventors: Collin Murray, Maynard, MA (US); Joseph King, Waltham, MA (US); Irina Pyataeva, Roxburry, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 101 days.

(21) Appl. No.: 16/666,678

(22) Filed: Oct. 29, 2019

(65) Prior Publication Data

US 2020/0155159 A1    May 21, 2020

Related U.S. Application Data

(60) Provisional application No. 62/767,816, filed on Nov. 15, 2018.

(51) Int. Cl.
  *A61B 17/128* (2006.01)
  *A61B 17/122* (2006.01)
  *A61B 17/12* (2006.01)

(52) U.S. Cl.
  CPC .......... *A61B 17/128* (2013.01); *A61B 17/122* (2013.01); *A61B 2017/12004* (2013.01)

(58) Field of Classification Search
  CPC ....... A61B 17/08; A61B 17/083; A61B 17/10; A61B 17/12; A61B 17/122; A61B 17/1227; A61B 17/128; A61B 17/1285; A61B 2017/12004
  See application file for complete search history.

(56) References Cited

U.S. PATENT DOCUMENTS

| | | | |
|---|---|---|---|
| 2002/0045909 A1* | 4/2002 | Kimura | A61B 17/083 606/151 |
| 2008/0140089 A1* | 6/2008 | Kogiso | A61B 17/1285 606/142 |
| 2011/0046651 A1 | 2/2011 | Cohen et al. | |
| 2011/0238093 A1* | 9/2011 | Matsuoka | A61B 17/1285 606/151 |

(Continued)

FOREIGN PATENT DOCUMENTS

EP   1 493 392   1/2005

*Primary Examiner* — Melanie R Tyson
(74) *Attorney, Agent, or Firm* — Fay Kaplun & Marcin, LLP

(57) ABSTRACT

A system for treating tissue includes a clip assembly including a pair of clip arms. Proximal ends of the clip arms are slidably received within a channel of a capsule to be moved between a tissue receiving configuration and a tissue clipping configuration. The system also includes a catheter assembly including a control member extending therethrough. The control member includes a distal end connected to the clip arms to move the clip assembly between the receiving and clipping configurations. The system further includes a coupler releasably coupled to a proximal end of the capsule and configured to be coupled to the distal end of the catheter assembly. The coupler fractures when a proximal force exerted on the coupler via the control member exceeds a first predetermined threshold value to disengage the capsule and deploy the clip assembly.

18 Claims, 2 Drawing Sheets

(56) References Cited

U.S. PATENT DOCUMENTS

2018/0085122 A1\* 3/2018 Ryan ................ A61B 17/1285
2018/0116677 A1   5/2018 Estevez et al.
2018/0153552 A1\* 6/2018 King ................. A61B 17/083

\* cited by examiner

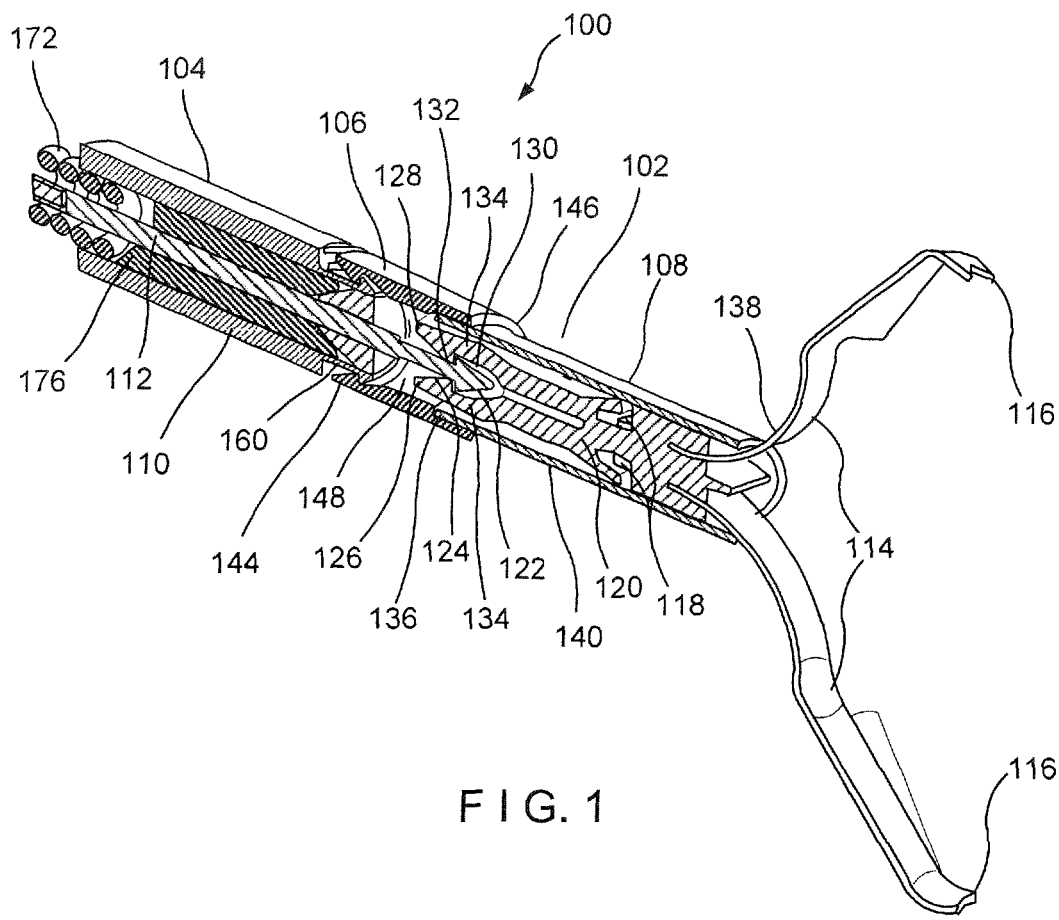
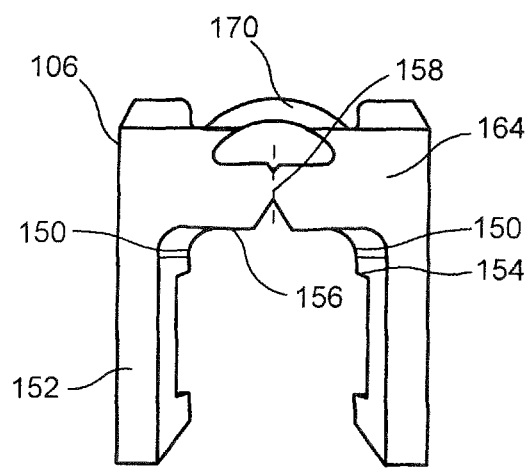
FIG. 2
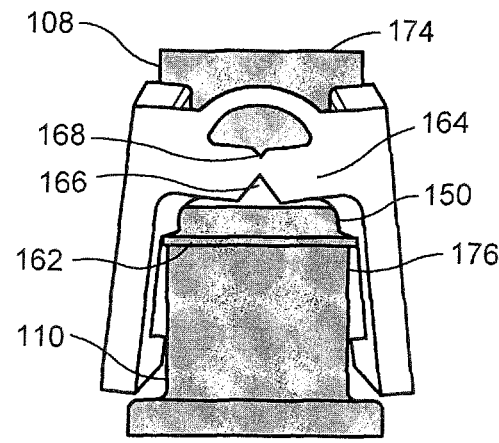
FIG. 3
FIG. 1

STRETCH HOOP COUPLER FOR RELOADABLE HEMOSTASIS CLIPPING DEVICE

PRIORITY CLAIM

The present disclosure claims priority to U.S. Provisional Patent Application Ser. No. 62/767,816 filed Nov. 15, 2018; the disclosure of which is incorporated herewith by reference.

FIELD

The present disclosure relates generally to medical clips, and more specifically, to hemostatic clips delivered to a target site through an endoscope.

BACKGROUND

Pathologies of the gastrointestinal (GI) system, the biliary tree, the vascular system, and other body lumen and hollow organs are often treated through endoscopic procedures, many of which require hemostasis to control internal bleeding. Hemostasis clips are often employed to control such internal bleeding. These clips grasp tissue surrounding a wound and hold edges of the wound together temporarily to allow natural healing processes to permanently close the wound. Specialized endoscopic clipping devices are often used to deliver clips to desired locations within the body after which the clip delivery device is withdrawn, leaving the clip within the body.

Often, hemostasis clips include a coupler that connects a clip to a delivery device. By design, the coupler breaks when the clip is deployed to free the clip from the delivery device. One challenge in using a coupler that breaks is that the broken pieces may be small enough that they can be suctioned into the working channel of the endoscope where they can become stuck. As a result, the pieces may stay in the endoscope even after a standard cleaning procedure has been performed, increasing the risk of contaminating the endoscope and infecting patients.

SUMMARY

The present disclosure relates to a system for treating tissue comprising a clip assembly including a pair of clip arms, each of the clip arms extending from a proximal end to a distal end, proximal ends of the clip arms slidably received within a channel of a capsule to be moved between a tissue receiving configuration, in which distal ends of the clip arms are separated from one another, and a tissue clipping configuration, in which distal ends of the clip arms are moved toward one another, a catheter assembly including a bushing and a control member extending therethrough, the control member including a distal end configured to be connected to the clip arms to move the clip assembly between the tissue receiving configuration and the tissue clipping configuration, and a coupler releasably coupled to a proximal end of the capsule and configured to be coupled to the distal end of the catheter assembly, the coupler configured to fracture when a proximal force exerted on the coupler via the control member exceeds a first predetermined threshold value to disengage the capsule and deploy the clip assembly.

In an embodiment, the proximal ends of the clip arms are connected to one another via a yoke releasably coupleable with an enlarged distal end of the control member.

In an embodiment, a proximal portion of the coupler includes a plurality of fingers mountable over a distal portion of the bushing to couple the coupler to the catheter assembly.

In an embodiment, the coupler includes two sets of V-notches diametrically opposed about a circumference of a distal portion of the coupler, each set of V-notches including a proximal V-notch extending from a proximal end of a wall of the coupler and a distal V-notch extending from a distal end of the wall of the coupler, the sets of V-notches configured to fracture when a proximal force exerted thereon exceeds a threshold value.

In an embodiment, the coupler includes a ramped portion configured to interact with a ridge extending about a circumference of an outer surface of the bushing such that, when a proximal force is exerted on the coupler, the ramped portion is moved proximally over the ridge, expanding the wall of the coupler and causing the V-notch portions to fracture.

In an embodiment, each set of V-notches includes a third V-notch extending into the wall of the coupler from an outer surface thereof.

In an embodiment, the coupler includes a loop portion extending from a first side of each set of V-notches to a second side of each-set of V-notches, the loop portion preventing the coupler from disengaging from the distal end of the bushing when the coupler fractures.

The present disclosure also relates to a system for treating tissue comprising a clip assembly including a pair of clip arms and a capsule, each of the clip arms extending from a proximal end to a distal end, proximal ends of the clip arms slidably received within a channel of the capsule to be moved between a tissue receiving configuration, in which distal ends of the clip arms are separated from one another, and a tissue clipping configuration, in which distal ends of the clip arms are moved toward one another, a catheter assembly including a control member extending therethrough, the control member including a distal end configured to be connected to the clip arms to move the clip assembly between the tissue receiving configuration and the tissue clipping configuration, and a coupler releasably coupled to a proximal end of the clip assembly and configured to be coupled to the distal end of the catheter assembly, the coupler configured to fracture to disengage the capsule and deploy the clip assembly.

In an embodiment, the catheter assembly includes a bushing at a distal end thereof, the bushing configured to be coupled to the proximal end of the coupler.

In an embodiment, the coupler includes two sets of V-notches diametrically opposed about a circumference of a distal portion of the coupler, each set of V-notches including a proximal V-notch extending from a proximal end of a wall of the coupler and a distal V-notch extending from a distal end of the wall of the coupler, the sets of V-notches configured to fracture when a proximal force exerted thereon exceeds a threshold value.

In an embodiment, the coupler includes a ramped portion configured to interact with a ridge extending about a circumference of an outer surface of the bushing such that, when a proximal force is exerted on the coupler, the ramped portion is moved proximally over the ridge, expanding the wall of the coupler and causing the V-notch portions to fracture.

In an embodiment, each set of V-notches includes a third V-notch extending into the wall of the coupler from an outer surface thereof.

In an embodiment, the coupler includes a loop portion extending from a first side of each set of V-notches to a second side of each set of V-notches, the loop portion preventing the coupler from disengaging from the distal end of the bushing when the coupler fractures.

In an embodiment, the proximal ends of the clip arms are connected to one another via a yoke releasably couplable with an enlarged distal end of the control member.

In an embodiment, a proximal portion of the coupler includes a plurality of fingers mountable over a distal portion of the bushing to couple the coupler to the catheter assembly.

The present disclosure also relates to a method of treating tissue comprising loading a clip assembly on a catheter assembly by coupling a proximal end of a coupler to a distal end of the catheter assembly and coupling a distal end of the coupler to a proximal end of the clip assembly, a control member of the catheter assembly being releasably connected to proximal ends of clip arms of the clip assembly, inserting the loaded clip assembly to a target site within a living body via a working channel of an insertion device, moving the clip assembly between a tissue receiving configuration, in which distal ends of the clip arms are separated from one another, and a tissue clipping configuration, in which distal ends of the clip arms are moved toward one another, by moving the control member longitudinally relative to the clip assembly until a target tissue is gripped therebetween, as desired, and releasing the clip assembly from the catheter by drawing the control member proximally relative to the clip arms, beyond a predetermined threshold value, so that the coupler yields to disengage the clip assembly and at least a portion of the coupler remains connected to the catheter assembly.

In an embodiment, the method further comprises drawing the control member further proximally, beyond a predetermined threshold value, until an enlarged distal end of the control member disengages from a yoke of the clip assembly.

In an embodiment, the proximal ends of the clip arms are connected to one another via a yoke releasably couplable with an enlarged distal end of the control member.

In an embodiment, the coupler includes two sets of V-notches diametrically opposed about a circumference of a distal portion of the coupler, each set of V-notches including a proximal V-notch extending from a proximal end of a wall of the coupler and a distal V-notch extending from a distal end of the wall of the coupler, the sets of V-notches configured to fracture when a proximal force exerted thereon exceeds a threshold value.

In an embodiment, the coupler includes a loop portion extending from a first side of each set of V-notches to a second side of each-set of V-notches, the loop portion preventing the coupler from disengaging from the distal end of the bushing when the coupler fractures.

BRIEF DESCRIPTION

FIG. 1 shows a perspective cross-sectional view of a clipping device according to an exemplary embodiment of the present disclosure;

FIG. 2 shows a perspective view of a hoop coupler of the clipping device of FIG. 1 according to an exemplary embodiment of the present disclosure;

FIG. 3 shows another perspective view of the hoop coupler of FIG. 1;

DETAILED DESCRIPTION

Figure 4:
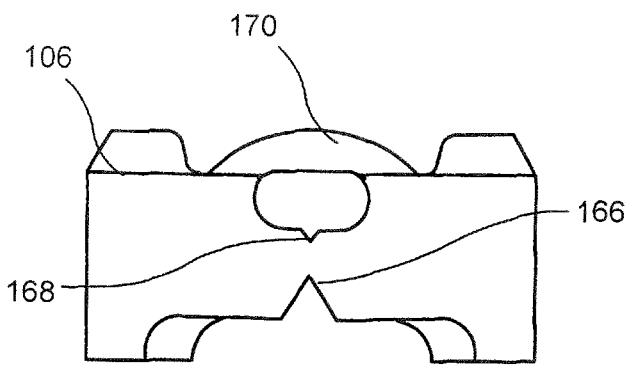
FIG. 4 shows a perspective view of a hoop coupler of a clipping device according to a second exemplary embodiment of the present disclosure.

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of a catheter assembly prior to an endoscopic procedure. Once a clip has been deployed at a desired target area in the body, the catheter assembly may be reloaded with a new clip. In particular, the catheter assembly includes a coupler for releasably coupling a bushing of the catheter assembly to a clip assembly so that multiple clips can be fired using a single catheter assembly. The coupler is pre-assembled with a proximal end of a capsule and is configured to be coupled to a distal end of the bushing. When it is desired to deploy the clip assembly in the body, the control member is drawn proximally with respect to the clip assembly until the coupler disengages from the capsule or fractures to release the capsule from the catheter assembly. In exemplary embodiments, the coupler includes a hoop designed to keep the fractured coupler on the tip of the catheter assembly when the coupler breaks. It should be noted that the terms "proximal" and "distal," as used herein, refer to a direction toward (proximal) and away from (distal) a user of the device.

As shown in FIG. 1, a system 100 according to an exemplary embodiment of the present disclosure comprises a clip assembly 102, a catheter assembly 104 and a coupler 106 facilitating a releasable connection between the catheter assembly 104 and the clip assembly 102. The clip assembly 102 is loadable onto a bushing 110 of the catheter assembly 104 prior to insertion of the system 100 into a living body for the clipping of target tissue. The catheter assembly 104 is configured such that, after deployment of the clip assembly 102 in the living body, a new clip assembly 102 may be loaded onto the catheter assembly 104 so that the same catheter assembly 104 may be used to deliver multiple clip assemblies 102 to further portions of target tissue in the living body. In this embodiment, a capsule 108 of the clip assembly 102 is pre-assembled with the coupler 106 and is configured to be releasably connected to the catheter assembly 104. Once the capsule 108 of the clip assembly 102 has been coupled to the bushing 110 of the catheter assembly 104, a control member 112 of the catheter assembly 104 releasably connected to clip arms 114 of the clip assembly 102 is movable longitudinally relative to the catheter assembly 104 and capsule 108 to move the clip assembly 102 between an open tissue receiving configuration in which distal ends 116 of the clip arms 114 are separated from one another to receive target tissue therebetween and a closed tissue gripping configuration in which the distal ends 116 are drawn toward one another to grip target tissue therebetween. Upon clipping of the target tissue, as desired, a compressive force may be exerted on the coupler 106 causing a portion of the coupler 106 of this embodiment to yield and/or fracture to release the capsule 108 from the catheter assembly 104. It is noted that although this exemplary embodiment is shown and described with a coupler 106 pre-assembled with the capsule 108 of the clip assembly 102, in another embodiment, the coupler 106 may be similarly pre-assembled with the bushing 110 of the catheter assembly 104 to be releasably connected to the capsule 108.

The clip assembly 102 includes a pair of clip arms 114, proximal ends 118 of which are connected to a yoke 120 slidably received within the capsule 108 so that, when the yoke 120 is coupled to the control member 112 of the catheter assembly 104 and the capsule 108 is coupled to the bushing of the catheter assembly 104 via the coupler 106, longitudinal motion of the control member 112 relative to the bushing 110 moves the clip assembly 102 between the tissue receiving and the tissue gripping configurations. The clip arms 114 of this embodiment are biased toward the open tissue receiving configuration so that, when not constrained by the capsule 108, the clip arms 114 move under their natural bias to the tissue receiving configuration with distal ends 116 of the clip arms 114 spread apart from one another. When the clip arms 114 are drawn into the capsule 108, the capsule 108 constrains the clip arms 114, holding the distal ends 116 together in the tissue gripping configuration.

Each of the clip arms 114, as noted above, extends from a proximal end 118 to a distal end 116. As would be understood by those skilled in the art, the clip arms 114 of this embodiment include optional gripping features configured to enhance the gripping of tissue therebetween. For example, the distal ends 116 of one or both of the clip arms 114 may include tips extending laterally inward toward the other clip arm 114 with the tips including, for example, teeth, protrusions, spikes or other structures) configured to grip tissue between the distal ends 116. One or both of the clip arms 114 may also include a locking feature configured to lock the clip arms 114 in the tissue gripping configuration after target tissue has been gripped as desired by the clip arms 114. In one embodiment, a proximal part of one or both of the clip arms 114 includes a locking tab extending laterally outward therefrom configured to engage a portion of the capsule 108 when the clip arms 114 have been drawn into the capsule 108 by a predetermined distance. For example, the locking tabs may be received within correspondingly sized, shaped and positioned locking windows extending laterally into or through a wall of the capsule 108 to lock the clip arms 114 relative to the capsule 108, in the tissue gripping configuration.

In one embodiment, the proximal ends 118 of the clip arms 114 are connected to one another to form one integral piece which is connected to the yoke 120. In another embodiment, the proximal ends 118 are formed as separate elements connected to one another via the yoke 120. The yoke 120 is connected to the proximal end 118 of each of the clip arms 114 and is configured to be releasably connected to an enlarged distal end 122 of the control member 112 of the catheter assembly 104. For example, the yoke 120 may include a longitudinal slot 124 extending from a proximal opening 126 at a proximal end 128 of the yoke 120 along a longitudinal axis of the yoke 120 to a distal portion 130 sized and shaped to receive the enlarged distal end 122 of the control member 112 of the catheter assembly 104. In one exemplary embodiment, the enlarged distal end 122 is configured as a ball received within a correspondingly sized and shaped socket of the distal portion 130. A proximal portion 132 of the slot 124 extending between the proximal opening 126 and the distal portion 130 has a cross-sectional area (e.g., diameter) smaller than a cross-sectional area of the distal portion 130. The slot 124 may be defined via opposed portions 134 that are spreadable to receive the enlarged distal end 122 and are biased toward one another so that, once the enlarged distal end 122 passes distally into the distal portion 130, the opposed portions 134 spring back to lock the enlarged distal end 122 within the distal portion 130, coupling the control member 112 to the yoke 120, Thus, longitudinal movement of the control member 112 relative to the capsule 108 controls movement of the clip arms 114 between the tissue receiving and the tissue clipping configurations. And, in deployment, as increased tension is imparted to the control member 112, this tension is applied by the enlarged end 122 against the proximal portion 132 of the slot 124 until the opposed portions 134 are moved apart from one another to allow the control member 112 to separate from the yoke 120 as the clip assembly 102 is deployed.

According to this embodiment, the enlarged distal end 122 of the control member 112 is inserted into the distal portion 130 via the proximal opening 126 of the yoke 120. When the control member 112 is pushed distally into the yoke 120 beyond a predetermined threshold value, the proximal opening 126 of the slot 124 deforms via separation of the opposed portions 134 to permit the enlarged distal end 122 to pass through the proximal portion 132 into the distal portion 130. Once the enlarged end 122 is received within the distal portion 130, the proximal portion 132 of the slot 124 reverts to its original size, holding the enlarged end 122 of the control member 112 in the distal portion 130.

The capsule 108 extends from a proximal end 136 to a distal end 138 and includes a channel 140 extending longitudinally therethrough. The channel 140 is sized and shaped to slidably receive the yoke 120 and at least proximal portions of the clip arms 114 therein. As described above, the capsule 108 may also include locking features (e.g., locking windows) for engaging corresponding locking features of the clip arms 114 (e.g., locking tabs). In this embodiment, the proximal end 136 may be pre-assembled with the coupler 106. The capsule 108 may include a window (not shown) extending laterally through the proximal end 136 thereof for receiving a correspondingly sized and shaped engaging feature of the coupler 106. In one embodiment, the capsule 108 includes a pair of diametrically opposed windows for engaging the coupler 106. It will be understood by those of skill in the art, however, that the capsule 108 may include any number of windows for receiving any number of corresponding engaging features of the coupler 106. It will also be understood by those of skill in the art that the coupler 106 may be pre-assembled with the capsule 108 via any one of a variety of couplings.

The coupler 106 extends from a proximal end 144 to a distal end 146 and includes a channel 148 extending therethrough. In an embodiment, as noted above, the distal end 146 of the coupler 106 may be pre-assembled with the proximal end 136 of the capsule 108 so that the channel 148 of the coupler 106 is in communication with the channel 140 of the capsule 108. Thus, the control member 112 of the catheter assembly 104 may be passed through the channels 148, 140 of the coupler 106 and the capsule 108, respectively, to be coupled to the yoke 120 during loading of the clip assembly 102. A proximal portion of the capsule 108 may be sized and shaped to be received within the channel 148 of the coupler 106 so that inwardly engaging features at a distal portion of the coupler 106 may be receive within the windows (not shown) of the capsule 108 to connect the coupler 106 thereto. In one embodiment, the coupler 106 includes a pair of opposing tabs (not shown) receive within diametrically opposing windows of the capsule 108. The coupler 106, however, may include any number of tabs for connecting the coupler 106 to the capsule 108.

A proximal portion of the coupler 106 of this embodiment includes a plurality of fingers 152 configured to engage the bushing 110 of the catheter assembly 104. The fingers 152 are mounted over a distal end 160 of the bushing 110 so that the bushing 110 and the coupler 106 are snap fit together. The fingers 152 are biased toward an engaging configuration but may be spread apart to permit the distal end 160 of the bushing 110 to be received therein. In particular, each of the fingers 152 includes a groove 153 extending along an interior surface thereof, the groove 153 sized and shaped to receive a corresponding engaging feature 162, or ridge, of the distal end 160 of the bushing 110. The ridge 162 extends about a circumference of an exterior surface of the bushing 110, as shown in FIG. 3. The fingers 152 deflect away from one another as the ridge 162 at the distal end 160 is being inserted therebetween. Once the ridge 162 is received within the grooves 153, however, the fingers 152 snap inward under their natural bias so that the grooves 153 and the ridge 162 engage one another, coupling the bushing 110 to the coupler 106. Each of the fingers 152 also includes a ramped portion 150 at a distal portion of the inner surface thereof, as shown in FIGS. 2-3. The ramped portion 150 has a thickness that increases from a proximal end 154 thereof to a distal end 156 thereof and is configured to interface with the ridge 162 on the exterior surface of the bushing 110, as will be described in further detail below.

A distal portion of a wall 164 of the coupler 106 includes two diametrically opposed sets of V-notches 158 configured to open (e.g., separate, break or fracture) to release the capsule 108 from the coupler 106. Specifically, each set of V-notches 158 includes a proximal V-notch 166 and a distal V-notch 168. The proximal V-notch 166 tapers from a proximal end to a distal end and the distal V-notch 168 tapers from a distal end to a proximal end such that the pointed ends of the V-notches 166, 168 are closest to one another. The sets of V-notches 158 are each configured to open (e.g., separate, fracture or break) when proximal force is applied thereto via proximal movement of the capsule 108. Thus, the coupler 106 is configured to open along two diametrically opposed longitudinal axes parallel to a central longitudinal axis of the coupler 106. The opening of the two V-notch sets 158 allows expansion of the distal end 146 of the coupler 106, allowing engaging features of the coupler 106 to be released form the windows of the capsule 108. To prevent the coupler 106 from being released from the bushing 110 of the catheter assembly 104, a pair of loop portions 170, positioned on a distal side of the wall 164, extend from a first side of the each of the V-notch sets 158 to a second side of each of the V-notch sets 158, as shown in FIGS. 2-3. Thus, when the V-notches 166, 168 open the coupler 106 is held together, about the bushing 110, by the loop portions 170.

Figure 5:
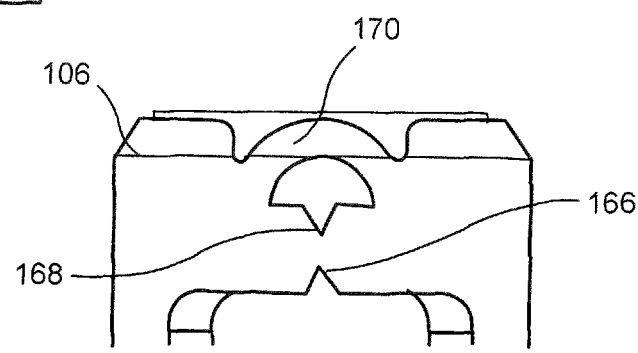
FIG. 5 shows a perspective view of a hoop coupler of a clipping device according to a third exemplary embodiment of the present disclosure.
Figure 6:
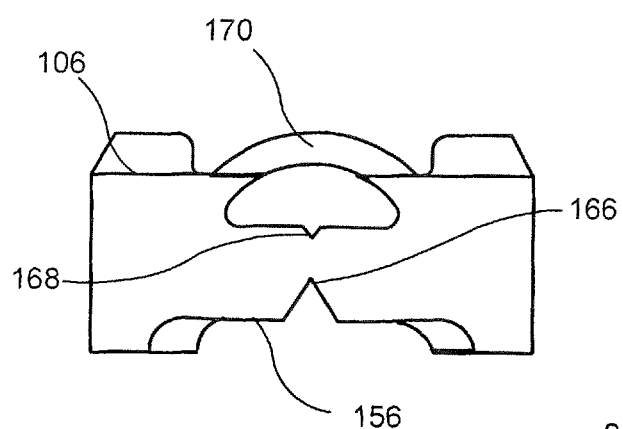
FIG. 6 shows a perspective view of a hoop coupler of a clipping device according to a fourth exemplary embodiment of the present disclosure.

As shown in FIGS. 4-6, the shape of each of the loop portions 170 may be changed based on the amount of deflection required for the coupler 106 to release the capsule 108. For example, in some instances, greater deflection, or outward expansion of the distal end 146 of the coupler 106 may be preferred. In other instances, lesser deflection may be preferred. To provide more deflection to the distal end of the coupler 106, the loop portions 170 may be formed of a flexible material such as, for example, an injection molded polymer, acrylic, polycarbonate, etc. Contrarily, loop portions 170 formed from more rigid materials will result in less expansion. In another embodiment, as shown in FIGS. 4-5, shorter loop portions 170 can be seen (as compared to loop portions 170 of FIG. 6), which result in less expansion of the coupler 106. In contrast, the loop portions 170 of FIG. 6, are longer in length, providing the coupler 106 with a greater degree of expansion. Furthermore, the size of the V-notches 166, 168 may be varied to increase or decrease the amount of deflection of the distal end 146 of the coupler 106. For example, a larger distal V-notch 168, as shown in FIG. 5, allows for more deflection of the distal end 146, without fracture, than smaller distal V-notches 168 shown in FIGS. 4 and 6.

The catheter assembly 104 includes the bushing 110, a flexible member 172 extending proximally therefrom, and the control member 112 extending longitudinally through the flexible member 172 and bushing 110. A proximal end (not shown) of the flexible member 172 may be connected to a handle portion. A proximal end (not shown) of the control member 112 in this embodiment is connected to an actuator of the handle portion so that the longitudinal movement of the control member 112 relative to the flexible member 172 and the bushing 110 may be controlled by a user at the handle portion.

The flexible member 172 may be formed as a coil of wire through which the control member 112 extends from the enlarged distal end 122 to the proximal end (not shown). As would be understood by those skilled in the art, the coil of wire preferably has sufficient flexibility to be passed through even tortuous paths of living body and, in this embodiment (e.g., it will have a flexibility enabling it to pass through a flexible endoscope along any path traversable by the endoscope) is sized and shaped to permit it to be passed through a working channel of an endoscope or other insertion device. Although the flexible member 172 is shown and described as a coil of wire, it will be understood by those of skill in the art that any other suitable flexible structure may be employed so long as the flexible member 172 is capable of providing a force in compression sufficient to counter the tension to be placed on the control member 112 from the clip assembly 102. As would be understood by those skilled in the art, the catheter assembly 104 may include any of a variety of actuating mechanisms for moving the control member 112 to control movement of the clip arms 114.

The bushing 110 extends longitudinally from a proximal end connected to the flexible member 172 to the distal end 160 configured to be releasably coupled to the coupler 106. The control member 112 extends through a lumen 174 of the bushing 110. A distal portion 176 of the bushing 110 may be sized and shaped to be inserted between the fingers 152 of the coupler 106 so that the ridge 162 at the distal end 160 of the bushing 110 is received and engaged with the grooves 153 of the fingers 152 of the coupler 106.

When it is desired to disengage the bushing 110 from the coupler 106 to deploy the clip assembly 102 in the body, the coupler 106 is moved proximally by drawing the control member 112 proximally relative thereto. Specifically, once the clip assembly 102 is locked in the tissue gripping configuration, proximal motion of the control member 112 draws the capsule 108 proximally, via the yoke 120, so that the coupler 106 is pulled proximally against the bushing 110. As the proximal force continues, the coupler 106 is drawn over the ridge 162 of the bushing 110 via the ramped portion 150. As the ramped portion 150 is drawn further proximally, the fingers 152 are deflected radially outward from a longitudinal axis of the coupler 106 by the outward force of the ridge 162 against the ramped portion 150, causing the V-notches 166, 168 to fracture. Fracturing of the V-notches 166, 168 allows the distal end 146 of the coupler 106 to expand, releasing the capsule 108. After the V-notches 166, 168 fracture, the loop portions 170 prevent the coupler 106 from breaking apart from the clip assembly 102 and hold the coupler 106 onto the bushing 110 so that the coupler 106 may be drawn out of the body with the catheter assembly 104.

An exemplary method for loading the clip assembly 102 onto the catheter assembly 104 comprises coupling the control member 112 to the yoke 120 and coupling the bushing 110 to the capsule 108 via the coupler 106. The enlarged distal end 122 of the control member 112 may be coupled to the clip arms 114 via the yoke 120 by pushing the enlarged distal end 122 distally against the proximal opening 126 of the yoke 120 until a distal force exerted thereon exceeds a predetermined threshold value, causing the oppose portions 134 thereof to deflect away from one another to permit the enlarged distal end 122 to be moved distally therepast into the distal portion 130 of the longitudinal slot 124. Once the enlarged distal end 122 is received within the distal portion 130, the opposing portions 134 revert to their original position, holding the enlarged distal end 122 within the yoke 120. The bushing 110 may be coupled to the capsule 108 via the coupler 106 by inserting a portion of the bushing 110 between the fingers 152 of the coupler 106 so that the coupler 106 and the bushing 110 engage one another via a snap fit. The proximal end 136 of the capsule 108 may be inserted into the distal end 146 of the coupler 106. Once the bushing 110 has been releasably connected to the capsule 108 and the enlarged distal end 122 is coupled to the yoke 120, the control member 112 may be moved proximally to draw the clip assembly 102 toward the closed, clipping configuration.

In use, after the clip assembly 102 has been loaded onto the catheter assembly 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted to the target tissue in the tissue gripping configuration to reduce damage and facilitate its passage through the working channel. Upon reaching the site of the target tissue, the clip assembly 102 is advanced out of the distal end of the working channel and the control member 112 is moved distally relative to the bushing 110 to extend the clip arms 114 distally out of the capsule 108 in to the tissue receiving configuration. Once the clip assembly 102 has been positioned so that target tissue is received between the clip arms 114, the clip assembly 102 is moved toward the tissue gripping configuration (by drawing the control member 112 proximally) so that the target tissue is gripped between the distal ends thereof. The clip arms 114 are moved toward the tissue gripping configuration by drawing the control member 112 proximally with respect to the bushing 110 and the capsule 108. Once the clip assembly 102 is in the tissue gripping configuration, the control member 112 is drawn further proximally to lock the clip arms 114 with respect to the capsule 108.

To deploy the clip assembly 102, the control member 112 is drawn proximally into the capsule until the coupler 106 attached to the capsule 108 is drawn proximally against the bushing 110. Further proximal motion of the coupler 106 causes the ridge 162 of the bushing 110 to slide distally against the ramped portion 150 of the coupling fingers 152 deflecting the fingers 152 radially outward. The coupler 106 is then moved even further proximally, causing the ridge 162 of the bushing 110 to expand the fingers 152 of the coupler 106 until tension applied to the V-notch sets 158 cause the V-notch sets 158 to open. Opening of the V-notch sets 158 allows the distal end of the coupler 106 to expand enough to release the capsule 108 therefrom while the loop portions 170 hold the fractured coupler 106 together and prevent the proximal end of the coupler 106 from expanding enough to be released from the distal end of the bushing 110.

Once the capsule 108 has disengaged from the coupler 106, the control member 112 is drawn even further proximally until the enlarged distal end 122 disengages from the yoke 120. In particular, when the force exerted on the yoke 120 by the enlarged distal end 122 exceeds a predetermined threshold value, opposed portions 134 spread apart, releasing the enlarged distal end therefrom. Alternatively, the yoke 120 may fracture to release the clip assembly 102 from the control member 112. The entire catheter assembly 104, including the control member 112 and the bushing 110, may then be withdrawn proximally from the body, leaving the clip assembly 102 (and any portions of the coupler 106 remaining attached thereto) clipped over the target tissue. The coupler 106 may be manually removed from the tip of the catheter assembly 104 and, if so desired, a new clip assembly 102 can be loaded onto the catheter assembly 104 in the same manner described above. This process may be repeated using the same catheter assembly 104 as many times as needed or desired.

Figure 7:
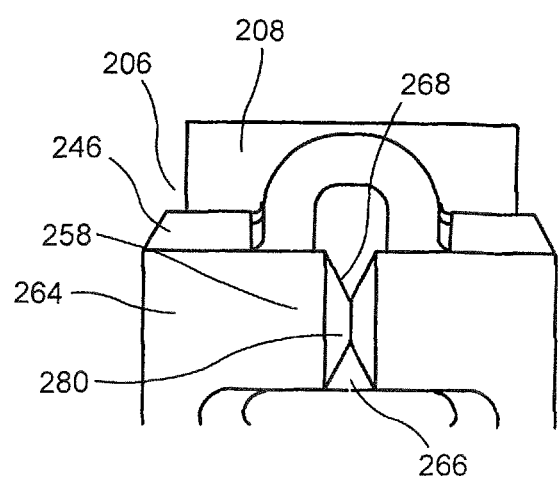
FIG. 7 shows a perspective view of a hoop coupler of a clipping device according to a fifth exemplary embodiment of the present disclosure.

As shown in FIG. 7, a coupler 206 according to another exemplary embodiment of the present disclosure is substantially similar to the coupler 106, except that each set of V-notches 258 includes a third v-notch 280 extending laterally into the wall 264. Specifically, as with coupler 106, the wall 264 of the coupler 206 includes two diametrically opposed sets of V-notches 258 configured to break or fracture to release the capsule 208 from the coupler 206. Specifically, each set of V-notches includes a proximal V-notch 266 and a distal V-notch 268. The proximal V-notch tapers from a proximal end to a distal end and the distal V-notch 268 tapers from a distal end to a proximal end such that the pointed ends of the V-notches 266, 268 are closest to one another. Additionally, as can be seen in FIG. 7, the sets of V-notches 258 include a third V-notch 280 is cut laterally into the wall 264. The third V-notch 280, as shown in the figure, extends from a proximal end of the wall 264 to a distal end of the wall 264, connecting the proximal and distal V-notches 266, 268. The third V-notch 280 only extends partially through the thickness of the wall 264 (i.e., a dimension extending perpendicular to a longitudinal axis of the coupler 206 between an inner and outer surface of the coupler 206). The depth of the third V-notch 280 into the wall 264 may vary depending on the preferred amount of force required to fracture the coupler 206. That is, the third V-notch 280 allows the user to have more control over the amount of force required to open the coupler 206. A shallower third V-notch 280 will require a greater amount of force than a deeper third V-notch 280. The sets of V-notches 258 are each configured to open (separate, fracture or break) when proximal compressive force is applied thereto via the capsule 208. Thus, the coupler 206 is configured to open along two diametrically opposed longitudinal axes parallel to a central longitudinal axis of the coupler 206. Opening of the two V-notch sets 258 allows expansion of the distal end 246 of the coupler 206, allowing the capsule 208 to be released from the coupler 206.

Although exemplary embodiments show and describe specific systems configured for loading clip assemblies onto an catheter assembly via a coupler, it will be understood by those of skill in the art that the present disclosure includes any variety of couplers for coupling a capsule of a clip assembly to an catheter assembly, so long as the coupler may be pre-assembled with the capsule and yields, fractures and/or is otherwise separable from the capsule during deployment of the clip assembly. Once the clip assembly has been deployed, the coupler (or a remaining portion thereof) may be removed from the bushing of the catheter assembly so that the catheter assembly may be loaded with a new clip assembly.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A system for treating tissue, comprising:
    a first clip assembly including a pair of clip arms, each of the clip arms extending from a proximal end to a distal end, proximal ends of the clip arms slidably received within a channel of a capsule to be moved between a tissue receiving configuration, in which distal ends of the clip arms are separated from one another, and a tissue clipping configuration, in which distal ends of the clip arms are moved toward one another;
    a catheter assembly including a bushing and a control member extending therethrough, the control member including a distal end configured to be connected to the clip arms to move the first clip assembly between the tissue receiving configuration and the tissue clipping configuration; and
    a first coupler releasably coupled to a proximal end of the capsule and configured to be coupled to the distal end of the catheter assembly, the first coupler configured to fracture when a proximal force exerted on the first coupler via the control member exceeds a first predetermined threshold value to disengage the capsule and deploy the first clip assembly,
    wherein a proximal portion of the first coupler includes a plurality of fingers mountable over a distal portion of the bushing to couple the first coupler to the catheter assembly.

2. The system of claim 1, wherein the proximal ends of the clip arms are connected to one another via a yoke releasably coupleable with an enlarged the distal end of the control member.

3. The system of claim 1, wherein the first coupler includes two diametrically opposed sets of V-notches on a distal portion of the first coupler, each set of V-notches including a proximal V-notch extending from a proximal end of a wall of the first coupler and a distal V-notch extending from a distal end of the wall of the first coupler, the sets of V-notches configured to fracture when a proximal force exerted thereon exceeds a threshold value.

4. The system of claim 3, wherein the first coupler includes a ramped portion configured to interact with a ridge extending about a circumference of an outer surface of the bushing such that, when a proximal force is exerted on the first coupler, the ramped portion is moved proximally over the ridge, expanding the wall of the first coupler and causing the V-notch portions to fracture.

5. The system of claim 3, wherein each set of V-notches includes a third V-notch extending into the wall of the first coupler from an outer surface thereof.

6. The system of claim 3, wherein the first coupler includes a loop portion extending from a first side of each set of V-notches to a second side of each-set of V-notches, the loop portion preventing the first coupler from disengaging from the distal end of the bushing when the first coupler fractures.

7. The system of claim 1, further comprising:
    a second coupler releasably coupled to a proximal end of a capsule of a second clip assembly, the second coupler configured to be coupled to the distal end of the catheter assembly after the first clip assembly has been deployed, the second coupler being configured to fracture when a proximal force exerted on the second coupler via the control member exceeds the first predetermined threshold value to disengage the capsule of the second clip assembly and deploy the second clip assembly.

8. The system of claim 1, wherein the distal end of the control member is enlarged.

9. A system for treating tissue, comprising:
    a clip assembly including a pair of clip arms, each of the clip arms extending from a proximal end to a distal end, proximal ends of the clip arms slidably received within a channel of a capsule to be moved between a tissue receiving configuration, in which distal ends of the clip arms are separated from one another, and a tissue clipping configuration, in which distal ends of the clip arms are moved toward one another;
    a catheter assembly including a control member extending therethrough, the control member including a distal end configured to be connected to the clip arms to move the clip assembly between the tissue receiving configuration and the tissue clipping configuration; and
    a coupler releasably coupled to a proximal end of the clip assembly and configured to be coupled to the distal end of the catheter assembly, the coupler configured to fracture to disengage the capsule and deploy the clip assembly,
    wherein a proximal portion of the coupler includes a plurality of fingers mountable over a distal portion of a bushing to couple the coupler to the catheter assembly.

10. The system of claim 9, wherein the coupler includes two diametrically opposed sets of V-notches on a distal portion of the coupler, each set of V-notches including a proximal V-notch extending from a proximal end of a wall of the coupler and a distal V-notch extending from a distal end of the wall of the coupler, the sets of V-notches configured to fracture when a proximal force exerted thereon exceeds a threshold value.

11. The system of claim 10, wherein the coupler includes a ramped portion configured to interact with a ridge extending about a circumference of an outer surface of the bushing such that, when a proximal force is exerted on the coupler, the ramped portion is moved proximally over the ridge, expanding the wall of the coupler and causing the V-notch portions to fracture.

12. The system of claim 10, wherein each set of V-notches includes a third V-notch extending into the wall of the first coupler from an outer surface thereof.

13. The system of claim 10, wherein the coupler includes a loop portion extending from a first side of each set of V-notches to a second side of each set of V-notches, the loop portion preventing the coupler from disengaging from the distal end of the bushing when the coupler fractures.

14. The system of claim 9, wherein the proximal ends of the clip arms are connected to one another via a yoke releasably coupleable with the distal end of the control member.

15. The system of claim 9, wherein the distal end of the control member is enlarged.

16. A system for treating tissue, comprising:
- a first clip assembly including a pair of first clip arms, each of the first clip arms extending from a proximal end to a distal end, proximal ends of the first clip arms slidably received within a channel of a first capsule to be moved between a tissue receiving configuration, in which distal ends of the first clip arms are separated from one another, and a tissue clipping configuration, in which distal ends of the first clip arms are moved toward one another;
- a catheter assembly including a bushing and a control member extending therethrough, the control member including a distal end configured to be connected to the first clip arms to move the first clip assembly between the tissue receiving configuration and the tissue clipping configuration;
- a first coupler releasably coupled to a proximal end of the first capsule and configured to be coupled to the distal end of the catheter assembly, the first coupler configured to fracture when a proximal force exerted on the first coupler via the control member exceeds a first predetermined threshold value to disengage the first capsule and deploy the first clip assembly;
- a second clip assembly including a pair of second clip arms, each of the second clip arms extending from a proximal end to a distal end, proximal ends of the second clip arms slidably received within a channel of a second capsule to be moved between a tissue receiving configuration, in which distal ends of the second clip arms are separated from one another, and a tissue clipping configuration, in which distal ends of the second clip arms are moved toward one another; and
- a second coupler releasably coupled to a proximal end of the second capsule and configured to be coupled to the distal end of the catheter assembly after the first clip assembly has been deployed from the catheter assembly, the second coupler configured to fracture when a proximal force exerted on the second coupler via the control member exceeds a first predetermined threshold value to disengage the second capsule and deploy the second clip assembly,
- wherein a proximal portion of the first coupler includes a plurality of fingers mountable over a distal portion of the bushing to couple the first coupler to the catheter assembly.

17. The system of claim 16, wherein each of the first and second couplers includes two diametrically opposed sets of V-notches on a distal portion thereof, each set of V-notches including a proximal V-notch extending from a proximal end of a wall of the distal portion and a distal V-notch extending from a distal end of the wall, the sets of V-notches configured to fracture when a proximal force exerted thereon exceeds a threshold value.

18. The system of claim 16, wherein a proximal portion of the second coupler includes a plurality of fingers mountable over a distal portion of the bushing to couple the second coupler to the catheter assembly.

* * * * *